(12) United States Patent
Couturier

(10) Patent No.: US 8,394,904 B2
(45) Date of Patent: Mar. 12, 2013

(54) PROCESS FOR PREPARING ALKOXYAMINES RESULTING FROM β-PHOSPHORATED NITROXIDES

(75) Inventor: Jean-Luc Couturier, Lyons (FR)

(73) Assignee: Arkema France, Colombes (FR)

( * ) Notice: Subject to any disclaimer, the term of this patent is extended or adjusted under 35 U.S.C. 154(b) by 36 days.

(21) Appl. No.: 12/668,250

(22) PCT Filed: Jul. 8, 2008

(86) PCT No.: PCT/FR2008/051277
§ 371 (c)(1),
(2), (4) Date: Apr. 21, 2010

(87) PCT Pub. No.: WO2009/010693
PCT Pub. Date: Jan. 22, 2009

(65) Prior Publication Data
US 2011/0046407 A1 Feb. 24, 2011

(30) Foreign Application Priority Data

Jul. 9, 2007 (FR) ..................................... 07 56339

(51) Int. Cl.
*C08F 2/06* (2006.01)
(52) U.S. Cl. ......................... 526/193; 526/217; 526/220
(58) Field of Classification Search .................. 526/193, 526/217, 220
See application file for complete search history.

(56) References Cited

U.S. PATENT DOCUMENTS

2006/0142511 A1 6/2006 Couturier et al.
2008/0061463 A1 3/2008 Guillot et al.

OTHER PUBLICATIONS

Bertin, et al. (Accession No. 145:421104), 2006, retrieved from CAPLUS.*

* cited by examiner

*Primary Examiner* — Shawquia Young
(74) *Attorney, Agent, or Firm* — RatnerPrestia

(57) ABSTRACT

The invention relates to an improved process for preparing alkoxyamines resulting from β-phosphorated nitroxides corresponding to the formula (I):

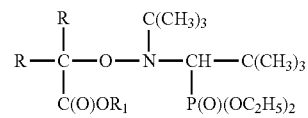

by reaction with a halogenated derivative in the presence of an organometallic system. This process comprises carrying out the reaction in a water-miscible organic solvent and precipitating the alkoxyamine directly from the organic medium by adding an aqueous solution of a strong acid. These alkoxyamines can be used in particular as radical polymerizations initiators.

13 Claims, No Drawings

PROCESS FOR PREPARING ALKOXYAMINES RESULTING FROM β-PHOSPHORATED NITROXIDES

TECHNICAL FIELD

A subject matter of the present invention is an improved process for the preparation of alkoxyamines resulting from β-phosphorated nitroxides by reaction, in a water-miscible organic solvent medium, with a halogenated derivative in the presence of an organometallic system. These alkoxyamines can be used in particular as initiators of radical polymerizations.

The alkoxyamines in the present invention correspond to the formula (I):

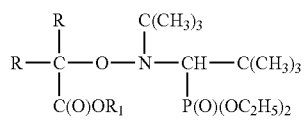

in which R represents a linear or branched alkyl radical having a number of carbon atoms ranging from 1 to 3 and $R_1$ represents a hydrogen atom, an alkali metal, such as Li, Na or K, or $NH_4^+$, $Bu_4N^+$ or $Bu_3NH^+$.

PRIOR ART AND TECHNICAL PROBLEM

The alkoxyamines corresponding to the formula (I), described in the document WO 04/014926, are initiators used for the polymerization and copolymerization of any monomer exhibiting a carbon-carbon double bond capable of polymerizing by the radical route.

Various synthetic routes are known from the literature for preparing alkoxyamines. The commonest method employs the coupling of a carbon-comprising radical with a nitroxide radical, in particular according to the method deploying the "ATRA" (Atom Transfer Radical Addition) reaction described in particular in the document WO 00/61544. This method consists in reacting a nitroxide with a halogenated derivative in the presence of an organometallic system, preferably based on copper. The reaction is carried out in a water-immiscible organic solvent, preferably aromatic hydrocarbons, such as benzene, toluene or xylenes, alkyl chlorides, such as dichloromethane, or ethers. Purification is carried out by washing the organic phase with water which may comprise a salt, such as, for example, an ammonium salt, followed by evaporation of the organic solvent under reduced pressure.

This process exhibits the disadvantage of producing large volumes of aqueous effluents comprising metals, in particular copper, necessitating subsequent treatments which are expensive and disadvantageous with regard to the productive output. Typically, the preparation of 2-methyl-2-[N-(tert-butyl)-N-(1-diethoxyphosphoryl-2,2-dimethylpropyl)aminoxy] propionic acid, carried out under the conditions described in example 1 of application WO 04/014926, generates 60 liters of aqueous effluents per kg of alkoxyamine obtained.

The problem to be solved is that of limiting the environmental risks related to the aqueous effluents, in particular by reducing their amounts, while maintaining the performance and the productive output of the process or even better still while improving them.

It has now been found, surprisingly, that it is possible to prepare the alkoxyamines corresponding to the formula (I) by carrying out the ATRA reaction in a water-miscible organic solvent. By virtue of the choice of the ligand of the organometallic system and by virtue of the specific structure of the alkoxyamine, it is then possible to very readily isolate the alkoxyamine directly by precipitation by addition of an acidic aqueous solution. This makes it possible to avoid tedious stages of washing with water and thus to reduce the amount of aqueous effluent while increasing the productive output.

ACCOUNT OF THE INVENTION

A subject matter of the invention is thus a process for the preparation of alkoxyamines of formula (I):

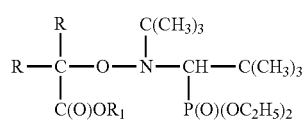

in which R represents a linear or branched alkyl radical having a number of carbon atoms ranging from 1 to 3 and $R_1$ represents a hydrogen atom, an alkali metal, such as Li, Na or K, or $NH_4^+$, $Bu_4N^+$ or $Bu_3NH^+$,
by reaction of the nitroxide of formula (II):

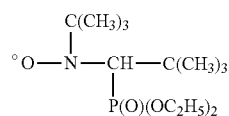

with a halocarbon compound of formula (III):

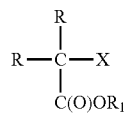

in which X represents a chlorine, bromine or iodine atom, preferably a bromine atom, and R and $R_1$ have the same meanings as in the formula (I),
in the presence of an organometallic system $MA(L)_n$ and/or $M(L)_n$ (IV),
in which M is a metal, such as Cu, Ag and/or Au, preferably Cu, A represents a halogen atom, a carboxylate group or a triflate group, preferably a chlorine atom or a bromine atom, L represents a ligand of the metal M,
characterized in that it is carried out in a water-miscible organic solvent and comprises the following stages:
 a) a metal salt MA and/or a metal M, the ligand L, the halocarbon compound of formula (III) and the nitroxide (II) are mixed with stirring in said solvent according to a compound (III)/nitroxide (II) molar ratio ranging from 1 to 1.5,
 b) the reaction medium is kept stirred at a temperature ranging from −10° C. to 60° C. until the nitroxide (II) has completely disappeared,
 c) an aqueous solution of a strong acid with a concentration ranging from 5 to 40% is added,
 d) the alkoxyamine (I) precipitated in stage c) is recovered by filtration.
Other characteristics and advantages of the invention will become apparent on reading the account which follows.

DETAILED ACCOUNT OF THE INVENTION

The process according to the invention makes it possible to obtain the alkoxyamines of formula (I) with fast kinetics and high yields under mild temperature conditions and with a halocarbon compound (III)/nitroxide (II) molar ratio close to stoichiometry, said alkoxyamine furthermore being precipitated directly from the reaction medium by addition of an acidic aqueous solution.

According to the present invention, use may be made, as water-miscible organic solvent, of protic solvents, such as alcohols, for example methanol, ethanol, 1-propanol or 2-propanol, or glycols, such as ethylene glycol or diethylene glycol, or polar aprotic solvents, such as ethers, for example tetrahydrofuran (THF), 1,4-dioxane or glycol ethers, for example diethylene glycol diethyl ether, acetone or acetonitrile.

Preferably, the solvent used is an alcohol, in particular methanol.

Generally, "water-miscible organic solvent" is understood to mean a solvent forming, in any proportion with water, a homogeneous, single-phase and transparent mixture.

According to the invention, the degree of oxidation of the active entity of the metal M is equal to 1 ($M^1$). This active entity can be added as such to the reaction medium, preferably in the form of a metal salt MA, more particularly a metal halide, such as CuBr.

According to another alternative form, it is also possible to introduce, into the reaction medium, a metal salt MA in which the metal M is in the oxidation state 1 and/or the same metal M in the oxidation state zero ($M^0$), copper being the preferred metal.

In a specific version of the process according to the invention, the metal M, in particular copper, is introduced into the reaction medium solely in the oxidation state 0, this making it possible to surprisingly reduce the amount of ligand necessary.

The ligand L is used according to an L/M molar ratio ranging from 1 to 5 and preferably ranging from 1 to 2.

The ligand of the metal M is chosen from polyamines, such as:

tris[2-(dimethylamino)ethyl]amine:

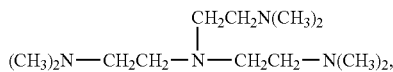

N,N',N',N",N"-pentamethyldiethylenetriamine (PMDETA):

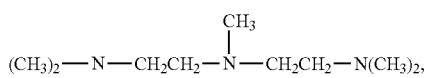

N,N,N',N'-tetramethylethylenediamine:

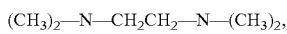

1,1,4,7,10,10-hexamethyltriethylenetetramine (HMTETA):

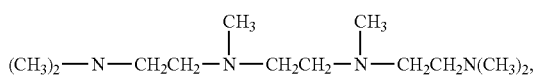

cyclic polyamines, such as:
1,4,7-trimethyl-1,4,7-triazacyclononane,
1,5,9-trimethyl-1,5,9-triazacyclododecane,
1,4,8,11-tetramethyl-1,4,8,11-tetraazacyclotetradecane.
Preferably, PMDETA will be used.

The process according to the invention generally consists in mixing the metal salt MA and/or the metal M with the ligand L at ambient temperature in the water-miscible organic solvent, and then the nitroxide (II) is added at ambient temperature. The halocarbon compound (III), with a compound (III)/nitroxide (II) molar ratio ranging from 1 to 1.5, preferably from 1 to 1.1, is introduced at the reaction temperature of between −10° C. and 60° C., preferably between 5° C. and 25° C.

The operation is preferably carried out under an atmosphere of inert gas, such as nitrogen or argon, and preferably at atmospheric pressure.

The reaction times are generally very short. The reaction end can be monitored by disappearance of the reactants, in particular the nitroxide, for example by chromatographic methods (GC, HPLC, TLC).

The duration of the reaction is determined by the complete disappearance of the nitroxide.

At the end of the reaction, the alkoxyamine (I) is precipitated from the organic medium by addition of an aqueous solution of a strong acid, such as hydrochloric acid. The concentration of the acidic solution is generally from 5 to 40%, preferably from 15 to 20%. The final pH of the reaction medium can range from 0.5 to 3, preferably from 1 to 2.

The alkoxyamine (I) is recovered by filtration. It can optionally be recrystallized by dissolution in an organic solvent, which can be the same as that used for the reaction, followed by precipitation with water.

The water-miscible organic solvent can be recycled by distillation. From this viewpoint, preference will be given to solvents which do not form a homoazeotrope with water, such as methanol.

The process according to the invention is particularly well suited to the manufacture of the alkoxyamine of formula (I) in which R is a methyl radical and $R_1$ is a hydrogen atom, sold by Arkema under the name BLOCBUILDER®, resulting in a reduced volume of aqueous effluent, typically from 8 to 10 liters/kg of alkoxyamine. Furthermore, the productive output is increased, the gain occurring both with regard to the reaction/purification time and with regard to the volume which can be used in the reactor.

The following examples illustrate the invention.

EXAMPLES

The tests are carried out under an inert gas (argon or nitrogen) atmosphere in a jacketed glass reactor of Schott type equipped with a mechanical stirrer of anchor type, a reflux condenser, a dropping funnel and a gas inlet.

The nitroxide of formula (II), called SG1, used as reactant was prepared by oxidation of diethyl 2,2-dimethyl-1-(1,1-dimethylamino)propylphosphonate with peracetic acid according to the process described in application EP 1 349 862.

The metal ligand used is N,N,N',N',N"-pentamethyldiethylenetriamine, hereinafter denoted PMDETA.

The solvents used, methanol, ethanol, isopropanol, acetone or acetonitrile, are degassed beforehand.

The compounds obtained are analyzed by $^1H$, $^{13}C$ and $^{31}P$ NMR for confirmation of the structure.

Example 1

Solvent Methanol 200 ml of degassed methanol and 91.9 g of PMDETA (0.530 mol, 1.8 equivalents) are charged to a 1 liter reactor purged with nitrogen. A mixture of 33.8 g of CuBr (0.236 mol, 0.8 equivalent) and 5.6 g of copper powder (0.088 mol, 0.3 equivalent) is introduced under a gentle nitrogen stream while maintaining the temperature at 20-25° C., followed by 86.4 g of SG1 (0.294 mol, 1 equivalent). The mixture is cooled to 5° C. and then 51.7 g of 2-bromo-2-methylpropionic acid (0.309 mol, 1.05 equivalents), dissolved in 100 ml of methanol, are run in over a period of 15 minutes. After the solution has finished being run in, reaction is allowed to take place at 5° C. for 30 minutes.

335 ml of an 18% aqueous hydrochloric acid solution are added while maintaining the temperature at 10-12° C. The final pH of the reaction medium is 1.8. Filtration is carried out in order to recover the crude alkoxyamine BlocBuilder®. The volume of copper-comprising effluent is 800 ml.

The alkoxyamine is recrystallized by dissolution in 330 ml of methanol and then reprecipitation by addition of 300 ml of water. The product is dried under vacuum at 40° C. 94 g of white powder (yield 84%) are obtained, the purity of which is confirmed by NMR analysis by comparison with the literature data.

Example 2

Solvent Methanol 50 ml of degassed methanol and 22.2 g of PMDETA (0.128 mol, 1.8 equivalents) are charged to a 250 ml reactor purged with nitrogen. A mixture of 8.2 g of CuBr (0.057 mol, 0.8 equivalent) and 1.36 g of copper powder (0.021 mol, 0.3 equivalent) is introduced under a nitrogen stream while maintaining the temperature at 20-25° C., followed by 21.1 g of SG1 (0.072 mol, 1 equivalent). 12.5 g of 2-bromo-2-methylpropionic acid (0.075 mol, 1.05 equivalents), dissolved in 25 ml of methanol, are run in dropwise at ambient temperature and then reaction is allowed to take place at ambient temperature for 4 hours.

Cooling is carried out to 10° C. and 110 ml of an 18% aqueous sulfuric acid solution are added. The final pH of the reaction medium is 1. Filtration is carried out and then the cake is washed with water. The product is dried under vacuum at 40° C. 23.3 g of white powder (yield 85%) are obtained. The analytical characteristics by NMR are identical to those of the alkoxyamine obtained in example 1.

Example 3

Solvent Methanol 50 ml of degassed methanol and 13.7 g of PMDETA (0.079 mol, 1.1 equivalents) are charged to a 250 ml reactor purged with nitrogen. 5 g of copper powder (0.079 mol, 1.1 equivalent) are introduced under a nitrogen stream while maintaining the temperature at 20-25° C., followed by 21.1 g of SG1 (0.072 mol, 1 equivalent). 12.5 g of 2-bromo-2-methylpropionic acid (0.075 mol, 1.05 equivalents), dissolved in 25 ml of methanol, are run in dropwise at ambient temperature and then reaction is allowed to take place at ambient temperature for 4 hours.

Cooling is carried out to 10° C. and 55 ml of an 18% aqueous hydrochloric acid solution are added. The final pH of the reaction medium is 1.5. Filtration is carried out and then the alkoxyamine is recrystallized by dissolution in 80 ml of methanol and reprecipitation by addition of 120 ml of water. The product is dried under vacuum at 40° C. 23.6 g of white powder (yield 86%) are obtained, the analytical characteristics of which by NMR are identical to those of the alkoxyamine obtained in example 1.

Example 4

Solvent Ethanol 200 ml of degassed ethanol and 104 g of PMDETA (0.600 mol, 2.2 equivalents) are charged to a 1 liter reactor purged with nitrogen. 34.1 g of CuBr (0.238 mol, 0.9 equivalent) and 3.8 g of copper powder (0.060 mol, 0.2 equivalent) are introduced under a nitrogen stream while maintaining the temperature at 20-25° C., followed by 79.2 g of SG1 (0.269 mol, 1 equivalent). The mixture is cooled to 5° C. and 50 g of 2-bromo-2-methylpropionic acid (0.299 mol, 1.1 equivalents), dissolved in 100 ml of ethanol, are run in dropwise; reaction is then allowed to take place at 5° C. for 4 hours.

340 ml of an 18% aqueous hydrochloric acid solution are added while maintaining the temperature at 5-10° C. Filtration is carried out and then the cake is washed with 3×250 ml of water. The product is dried under vacuum at 40° C. 87 g of white powder corresponding to the alkoxyamine of example 1 are obtained with a yield of 85%.

Example 5

Solvent Isopropanol 200 ml of degassed isopropanol and 109 g of PMDETA (0.629 mol, 2.2 equivalents) are charged to a 2 l reactor purged with nitrogen. 32.8 g of CuBr (0.229 mol, 0.8 equivalent) and 5.4 g of copper powder (0.085 mol, 0.3 equivalent) are introduced under a nitrogen stream while maintaining the temperature at 20-25° C., followed by 84.0 g of SG1 (0.285 mol, 1 equivalent). The mixture is cooled to 5° C. and 50 g of 2-bromo-2-methylpropionic acid (0.299 mol, 1.05 equivalents), dissolved in 100 ml of isopropanol, are run in dropwise; reaction is then allowed to take place at 5° C. for 4 hours.

710 ml of a 10% aqueous hydrochloric acid solution are added while maintaining the temperature at 10-12° C., followed by 200 ml of water. Filtration is carried out and then the cake is washed with water. The product is dried under vacuum at 40° C. 90 g of white powder corresponding to the alkoxyamine of example 1 are obtained with a yield of 82%.

Example 6

Solvent Acetone 50 ml of degassed acetone and 22.2 g of PMDETA (0.128 mol, 1.8 equivalents) are charged to a 250 ml reactor purged with nitrogen. 8.2 g of CuBr (0.057 mol, 0.8 equivalent) and 1.4 g of copper powder (0.022 mol, 0.3 equivalent) are introduced under a nitrogen stream while maintaining the temperature at 20-25° C., followed by 21.0 g of SG1 (0.071 mol, 1 equivalent). The mixture is cooled to 5° C. and 12.5 g of 2-bromo-2-methylpropionic acid (0.075 mol, 1.05 equivalents), dissolved in 25 ml of acetone, are run in dropwise; reaction is then allowed to take place at 5° C. for 4 hours.

80 ml of an 18% aqueous hydrochloric acid solution are added while maintaining the temperature at 10-12° C., followed by 40 ml of water. Filtration is carried out and then the cake is washed with water. The product is dried under vacuum at 40° C. 21.9 g of white powder corresponding to the alkoxyamine of example 1 are obtained with a yield of 81%.

Example 7

Solvent Acetonitrile 50 ml of degassed acetonitrile and 22.2 g of PMDETA (0.128 mol, 1.8 equivalents) are charged to a 250 ml reactor purged with nitrogen. 8.2 g of CuBr (0.057 mol, 0.8 equivalent) and 1.4 g of copper powder (0.022 mol, 0.3 equivalent) are introduced under a nitrogen stream while maintaining the temperature at 20-25° C., followed by 21.0 g of SG1 (0.071 mol, 1 equivalent). The mixture is cooled to 5° C. and 12.5 g of 2-bromo-2-methylpropionic acid (0.075 mol, 1.05 equivalents), dissolved in 25 ml of acetonitrile, are run in dropwise; reaction is then allowed to take place at 5° C. for 4 hours.

80 ml of an 18% aqueous hydrochloric acid solution are added while maintaining the temperature at 10-12° C., followed by 50 ml of water. Filtration is carried out and then the alkoxyamine is recrystallized by dissolution in 100 ml of methanol and reprecipitation by addition of 100 ml of water. The product is dried under vacuum at 40° C. 21 g of white powder corresponding to the alkoxyamine of example 1 are obtained with a yield of 77%.

What is claimed is:

1. A process for the preparation of alkoxyamines of formula (I):

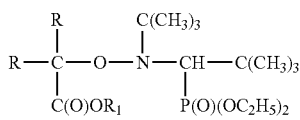

in which R represents a linear or branched alkyl radical having a number of carbon atoms ranging from 1 to 3 and $R_1$ represents a hydrogen atom, an alkali metal, $NH_4^+$, $Bu_4N^+$ or $Bu_3NH^+$, by reaction of the nitroxide of formula (II):

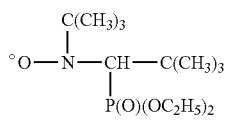

with a halocarbon compound of formula (III):

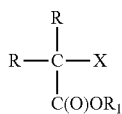

in which X represents a chlorine, bromine or iodine atom, and R represents a linear or branched alkyl radical having a number of carbon atoms ranging from 1 to 3 and $R_1$ represents a hydrogen atom, an alkali metal, $NH_4^+$, $Bu_4N^+$ or $Bu_3NH^+$, in the presence of an organometallic system $MA(L)_n$ and/or $M(L)_n$ (IV), in which M is a metal selected from the group consisting of Cu, Ag, Au and mixtures thereof, A represents a halogen atom, a carboxylate group or a triflate group, L represents a ligand of the metal M, and n is 1 to 5, characterized in that it is carried out in a water-miscible organic solvent and comprises the following stages:

a) mixing, with stirring, in said solvent, a metal salt MA and/or a metal M, the ligand L, the halocarbon compound of formula (III) and the nitroxide (II) at a compound (III)/nitroxide (II) molar ratio ranging from 1 to 1.5, b) maintaining, with stirring, the reaction medium at a temperature ranging from −10° C. to 60° C. until the nitroxide (II) has completely disappeared, c) adding an aqueous solution of a strong acid with a concentration ranging from 5 to 40%, d) recovering an alkoxyamine (I) from stage c) by filtration.

2. The process as claimed in claim 1, characterized in that the water-miscible organic solvent is a protic solvent selected from the group consisting of alcohols and glycols, or a polar aprotic solvent selected from the group consisting of ethers and glycol ethers.

3. The process as claimed in claim 1, characterized in that the compound (III)/nitroxide (II) molar ratio ranges from 1 to 1.1.

4. The process as claimed in claim 1, characterized in that the temperature ranges from 5 to 25° C.

5. The process as claimed in claim 1, characterized in that the metal M is introduced into the reaction medium in the oxidation state 0.

6. The process as claimed in claim 1, characterized in that the alkoxyamine is 2-methyl-2-[N-(tert-butyl)-N-(1-diethoxyphosphoryl-2,2-dimethylpropyl)aminoxy]propionic acid.

7. The process of claim 1, characterized in that the alkali metal is selected from the group consisting of Li, Na and K.

8. The process of claim 1, characterized in that the halogen A is selected from the group consisting of chlorine and bromine.

9. The process of claim 2, characterized in that the alcohol is selected from the group consisting of methanol, ethanol, 1-propanol and 2-propanol.

10. The process of claim 2 characterized in that the glycol is selected from the group consisting of ethylene glycol and diethylene glycol.

11. The process of claim 2, characterized in that the ether is selected from the group consisting of tetrahydrofuran (THF) and 1,4-dioxane.

12. The process of claim 2, characterized in that the glycol ether is selected from the group consisting of diethylene glycol diethyl ether, acetone and acetonitrile.

13. The process of claim 5, characterized in that the metal M is copper.

* * * * *